United States Patent
Sato

(10) Patent No.: US 10,163,196 B2
(45) Date of Patent: Dec. 25, 2018

(54) IMAGE PROCESSING DEVICE AND IMAGING SYSTEM

(71) Applicant: OLYMPUS CORPORATION, Tokyo (JP)

(72) Inventor: Tomoya Sato, Tokorozawa (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/640,639

(22) Filed: Jul. 3, 2017

(65) Prior Publication Data

US 2017/0301069 A1 Oct. 19, 2017

Related U.S. Application Data

(63) Continuation of application No. PCT/JP2016/066798, filed on Jun. 6, 2016.

(30) Foreign Application Priority Data

Jun. 30, 2015 (JP) .................................. 2015-131743

(51) Int. Cl.
*G06T 5/00* (2006.01)
*G02B 23/24* (2006.01)
(Continued)

(52) U.S. Cl.
CPC ............ *G06T 5/007* (2013.01); *A61B 1/0005* (2013.01); *A61B 1/00009* (2013.01);
(Continued)

(58) Field of Classification Search
CPC ................ G09G 2360/16; G06T 5/002; G06T 2207/10024; G06T 2207/20208;
(Continued)

(56) References Cited

U.S. PATENT DOCUMENTS 8,111,941 B2 * 2/2012 Kokemohr .............. G06T 5/009
358/3.26
8,339,475 B2 12/2012 Atanassov et al.
(Continued)

FOREIGN PATENT DOCUMENTS

JP 2000-023183 A 1/2000
JP 2012-093965 A 5/2012
(Continued)

OTHER PUBLICATIONS

International Search Report dated Aug. 23, 2016 issued in PCT/JP2016/066798.

*Primary Examiner* — Andrew Moyer
*Assistant Examiner* — Dennis Rosario
(74) *Attorney, Agent, or Firm* — Scully, Scott, Murphy & Presser, P.C.

(57) ABSTRACT

An image processing device includes: an HDR image generating unit configured to generate an HDR image signal by first high dynamic range combining of a first signal including first image data and a second signal including second image data; a tone compressing unit configured to generate a first tone-compressed image signal to be displayed by performing tone compression processing on the HDR image signal generated by the HDR image generating unit; and a color correcting unit configured to generate a second tone-compressed image signal by second high dynamic range combining of at least the first and second signals based on the first tone-compressed image signal.

1 Claim, 3 Drawing Sheets

(51) Int. Cl.
*A61B 1/00* (2006.01)
*A61B 1/04* (2006.01)
*A61B 1/06* (2006.01)
*G06T 1/20* (2006.01)
*G06T 5/50* (2006.01)

(52) U.S. Cl.
CPC ............ *A61B 1/041* (2013.01); *A61B 1/0684* (2013.01); *G02B 23/24* (2013.01); *G06T 1/20* (2013.01); *G06T 5/009* (2013.01); *G06T 5/50* (2013.01); A61B 1/0638 (2013.01); G02B 23/2484 (2013.01); G06T 2207/10024 (2013.01); G06T 2207/10068 (2013.01); G06T 2207/10144 (2013.01); G06T 2207/20208 (2013.01); G06T 2207/20221 (2013.01)

(58) Field of Classification Search
CPC ......... G06T 5/009; G06T 5/008; G06T 5/007; H04N 5/235; H04N 5/2355; H04N 9/045; H04N 5/35554; H04N 5/35581
See application file for complete search history.

(56) References Cited

U.S. PATENT DOCUMENTS

| | | | | |
|---|---|---|---|---|
| 8,447,132 | B1* | 5/2013 | Galil | G06K 9/00228 |
| | | | | 358/1.9 |
| 8,675,984 | B2* | 3/2014 | Jia | H04N 5/235 |
| | | | | 348/229.1 |
| 9,437,171 | B2* | 9/2016 | Narasimha | G09G 5/377 |
| 9,843,738 | B2* | 12/2017 | Cremers | H04N 5/2355 |
| 2017/0061584 | A1* | 3/2017 | Lim | G06T 5/002 |

FOREIGN PATENT DOCUMENTS

| | | | | |
|---|---|---|---|---|
| JP | 2012-513172 A | 6/2012 | | |
| JP | 2015-073772 A | 4/2015 | | |
| JP | WO 2017002544 A1 * | 1/2017 | ............ | G02B 23/24 |

* cited by examiner

IMAGE PROCESSING DEVICE AND IMAGING SYSTEM

CROSS-REFERENCE TO RELATED APPLICATIONS

This application is a continuation of PCT international application Ser. No. PCT/JP2016/066798 filed on Jun. 6, 2016 which designates the United States, incorporated herein by reference, and which claims the benefit of priority from Japanese Patent Application No. 2015-131743, filed on Jun. 30, 2015, incorporated herein by reference.

BACKGROUND

1. Technical Field

The disclosure relates to relates to an image processing device and an imaging system that perform combining processing of image signals having different brightness.

2. Related Art

In recent years, technique to generate a high dynamic range (HDR) image a dynamic range of which is expanded by combining input images having different brightness (exposure amounts) and then to generate a tone-compressed image that can be displayed on a monitor by performing tone compression processing on this HDR image is known (e.g. see Japanese Unexamined Patent Publication (Translation of PCT Application) No. 2012-513172).

SUMMARY

In some embodiments, an image processing device includes: an HDR image generating unit configured to generate an HDR image signal by first high dynamic range combining of a first signal including first image data and a second signal including second image data; a tone compressing unit configured to generate a first tone-compressed image signal to be displayed by performing tone compression processing on the HDR image signal generated by the HDR image generating unit; and a color correcting unit configured to generate a second tone-compressed image signal by second high dynamic range combining of at least the first and second signals based on the first tone-compressed image signal.

In some embodiments, an imaging system includes: an imaging device including a plurality of pixels configured to perform photoelectric conversion on external light, the imaging device being configured to generate first and second imaging signals having different exposure amounts; an HDR image generating unit configured to generate an HDR image signal by first high dynamic range combining of the first and second imaging signals; a tone compressing unit configured to generate a first tone-compressed image signal to be displayed by performing tone compression processing on the HDR image signal generated by the HDR image generating unit; and a color correcting unit configured to generates a second tone-compressed image signal by second high dynamic range combining of at least the first and second signals based on the first tone-compressed image signal.

The above and other features, advantages and technical and industrial significance of this disclosure will be better understood by reading the following detailed description of presently preferred embodiments of the disclosure, when considered in connection with the accompanying drawings.

DETAILED DESCRIPTION

An embodiment for carrying out the disclosure (hereinafter referred to as "embodiment") will be described below. In the embodiment, as an exemplary imaging system including an image processing device of the disclosure, an endoscope device for medical use that captures and displays an in-vivo image of a patient or the like. The disclosure is not limited by the embodiment. In descriptions of the drawings, the same part is denoted by the same symbol and thereby described.

Figure 1:
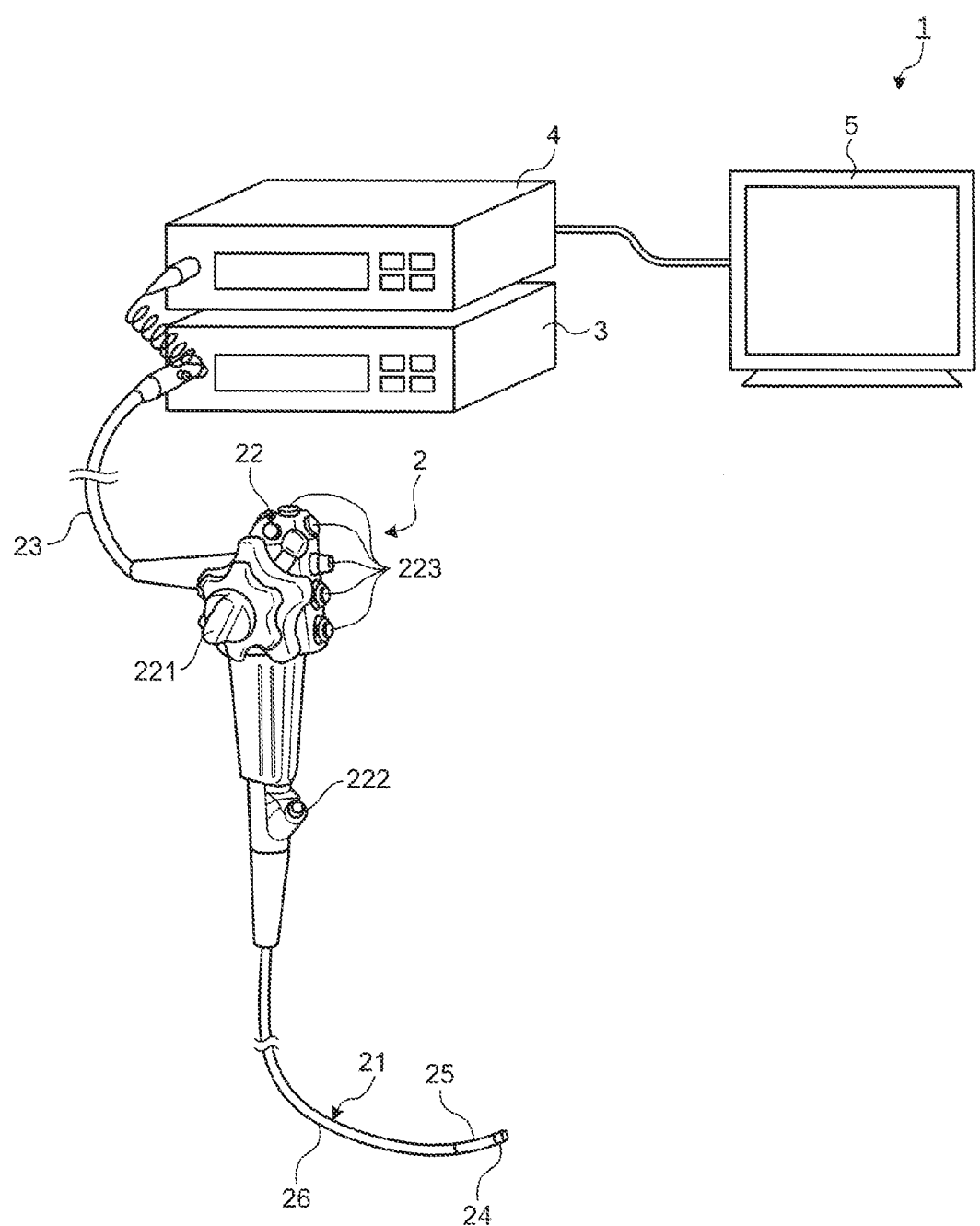
FIG. 1 is a diagram illustrating a schematic configuration of an endoscope system according to an embodiment of the disclosure.
Figure 2:
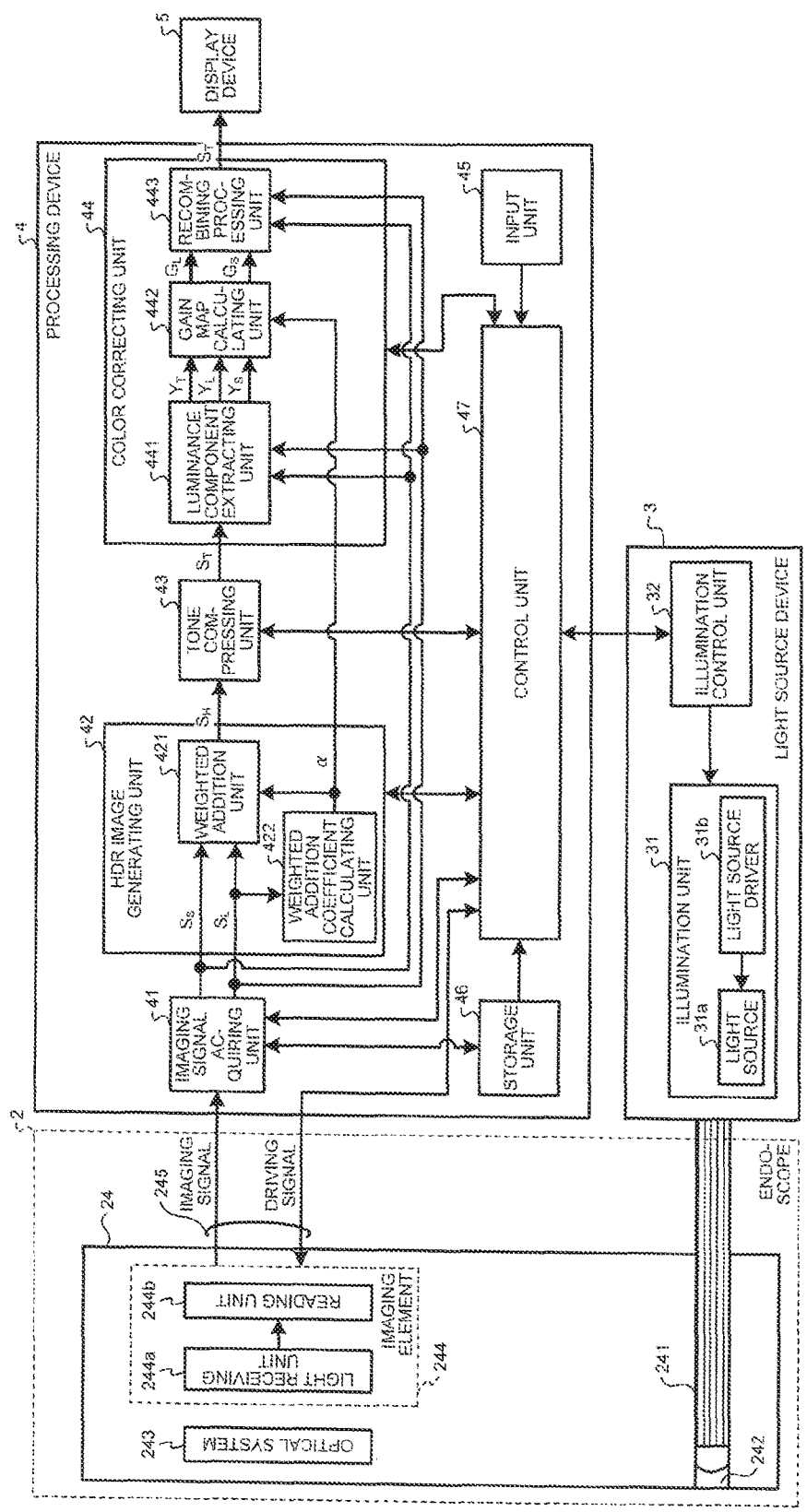
FIG. 2 is a block diagram illustrating a schematic configuration of the endoscope system according to the embodiment of the disclosure.

FIG. 1 is a diagram illustrating a schematic configuration of an endoscope system according to an embodiment of the disclosure. FIG. 2 is a block diagram illustrating a schematic configuration of the endoscope system according to the embodiment of the disclosure.

An endoscope system 1 illustrated in FIGS. 1 and 2 includes: an endoscope 2 that captures an in-vivo image of a subject by insertion of a distal end part in the subject; a light source device 3 that generates illumination light to be emitted from a distal end of the endoscope 2; a processing device 4 that performs predetermined signal processing on an imaging signal captured by the endoscope 2 and generally controls overall operation of the endoscope device 1; and a display device 5 that displays the in-vivo image generated by the signal processing by the processing device 4.

The endoscope 2 includes: an insertion unit 21 that is flexible and has a long thin shape; an operating unit 22 connected to a proximal end side of the insertion unit 21 and receives input of various operation signals; and a universal cord 23 extending in a different direction from a direction in which the insertion unit 21 extends from the operating unit 22 and incorporates various cables connected to the light source device 3 and the processing device 4.

The insertion unit 21 includes: a distal end part 24 incorporating an imaging element 244 (imaging device) arrayed with, in a two-dimensional shape, pixels that receive light and generate a signal by performing photoelectric conversion; a bending part 25 freely bendable and formed by a plurality of bending pieces; and a flexible pipe part 26 being flexible and long and connected to a proximal end side of the bending part 25. The insertion unit 21 is inserted in a body cavity of a subject and captures, by the imaging element 244, an object such as a biological tissue at a position where external light dose not reach.

The distal end part 24 includes: a light guide 241 formed by a glass fiber or the like and forming a light guiding path of light emitted by the light source device 3; an illumination lens 242 provided at a distal end of the light guide 241; an optical system 243 for condensing light; and the imaging element 244, included at an image formation position of the optical system 243, which receives light condensed by the optical system 243 and performs predetermined signal processing by photoelectric conversion into an electric signal.

The optical system 243 is formed by one or more lenses and has an optical zoom function to change the angle of view and a focus function to change the focus.

The imaging element 244 performs photoelectric conversion on light from the optical system 243 and thereby generates an electric signal (imaging signal). Specifically, the imaging element 244 includes a light receiving unit 244a and a reading unit 244b. The light receiving unit 244a is arrayed, in a matrix shape, with a plurality of pixels each of which includes a photodiode that accumulates electric charge corresponding to a quantity of light, a capacitor that converts the electric charge transferred from the photodiode into a voltage level, or other elements and generates an electric signal by performing photoelectric conversion on light from the optical system 243. The reading unit 244b sequentially reads electric signals generated by any pixel set as a reading target out of the plurality of pixels in the light receiving unit 244a and outputs as imaging signals. The imaging element 244 controls various operations of the distal end part 24 according to a driving signal received from the processing device 4. The imaging element 244 is implemented by a charge coupled device (CCD) image sensor, a complementary metal oxide semiconductor (CMOS) image sensor, or other sensors.

The operating unit 22 includes: a bending knob 221 that causes the bending part 25 to bend in the vertical direction and the horizontal direction; a treatment tool insertion unit 222 that inserts a treatment tool such as forceps, an electric scalpel, and an inspection probe in body cavity of a subject; and a plurality of switches 223 which are operation input units for inputting an operation command signal to peripheral devices such as an air delivering unit, a water delivering unit, and a screen display control in addition to the processing device 4 and the light source device 3. A treatment tool inserted from the treatment tool insertion unit 222 is exposed from an opening (not illustrated) via a treatment tool channel (not illustrated) of the distal end part 24.

The universal cord 23 incorporates at least a light guide 241 and a collective cable 245 where one or more signal wires are bundled. The collective cable 245 includes a signal wire for transmitting an imaging signal, a signal wire for transmitting a driving signal for driving the imaging element 244, and a signal wire for transmitting and receiving information including unique information related to the endoscope 2 (imaging element 244).

Next, a configuration of the light source device 3 will be described. The light source device 3 includes an illumination unit 31 and an illumination control unit 32. The illumination unit 31 sequentially switches a plurality of rays of illumination light having different exposure amounts and thereby emits the illumination light to an object (subject) under control by the illumination control unit 32. The illumination unit 31 includes a light source 31a and a light source driver 31b.

The light source 31a is formed by an LED light source that emits white light, one or more lenses, or other elements. The light source 31a emits light (illumination light) driven by the LED light source. Illumination light generated by the light source 31a is emitted toward an object from a distal end of the distal end part 24 via the light guide 241. Note that the light source 31a may be formed by a red LED light source, a green LED light source, and a blue LED light source. The light source 31a may emit, as illumination light, light having any wavelength band of red light, green light, and blue light.

The light source driver 31b supplies a current to the light source 31a under control by the illumination control unit 32 and thereby causes the light source 31a to emit illumination light.

The illumination control unit 32 controls the amount of electric power supplied to the light source 31a and further controls a driving timing of the light source 31a based on a control signal from the processing device 4. Under control by the illumination control unit 32, the illumination unit 31 exposes an object by each of first exposure processing for exposing with a first exposure amount and second exposure processing for exposing with a second exposure amount different from the first exposure amount. In the present embodiment, descriptions are given assuming that the first exposure amount is larger than the second exposure amount. The illumination control unit 32 adjusts the exposure amount by varying illumination intensity of illumination light, for example.

Next, a configuration of the processing device 4 will be described. The processing device 4 includes an imaging signal acquiring unit 41, a high dynamic range (HDR) image generating unit 42, a tone compressing unit 43, a color correcting unit 44, an input unit 45, a storage unit 46, and a control unit 47. Note that the HDR image generating unit 42, the tone compressing unit 43, and the color correcting unit 44 form the image processing device.

Figure 3:
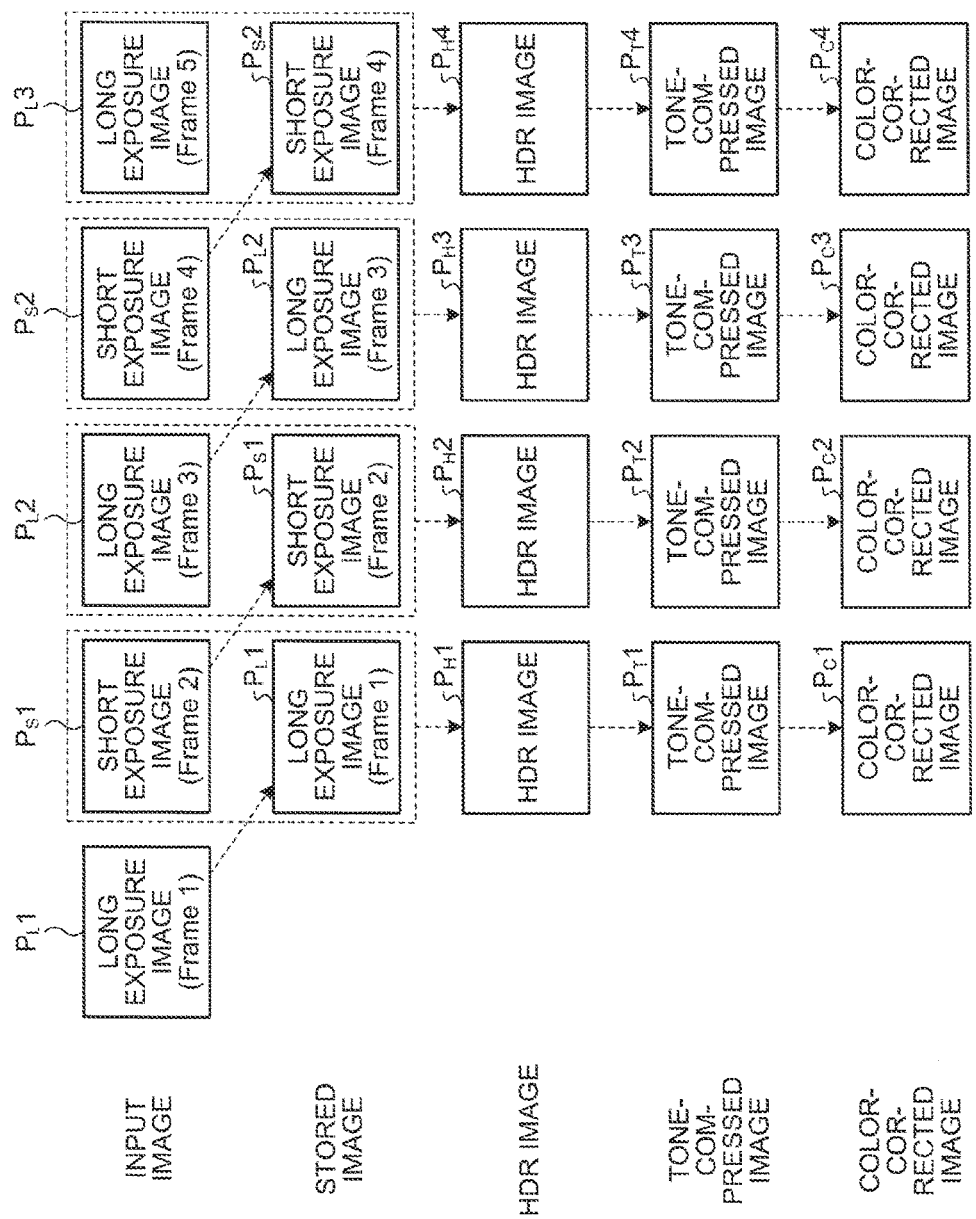
FIG. 3 is a schematic diagram explaining image generation by the endoscope system according to the embodiment of the disclosure.

The imaging signal acquiring unit 41 receives, from the endoscope 2, an imaging signal output from the imaging element 244. FIG. 3 is a schematic diagram explaining image generation by the endoscope system according to the embodiment of the disclosure. The imaging signal acquiring unit 41 generates an imaging signal including an input image (image data) by performing signal processing such as noise elimination, A/D conversion, synchronization processing (for example, performed when an imaging signal is acquired for each color component using a color filter or the like) on the acquired imaging signal. The imaging signal acquiring unit 41 generates, as input images, long exposure images $P_L1$ to $P_L3$ acquired by long exposure processing that is the first exposure processing and short exposure images $P_S1$ and $P_S2$ acquired by short exposure processing that is the second exposure processing and stores the generated input images in the storage unit 46. Each of the input images is provided with color components of red (R), green (G), or blue (B) by the signal processing. In FIG. 3, descriptions are given assuming that the imaging signal acquiring unit 41 acquires the long exposure image $P_L1$, the short exposure image $P_S1$, the long exposure image $P_L2$, the short exposure image $P_S2$, and the long exposure image $P_L3$ in the order mentioned.

The imaging signal acquiring unit 41 outputs, to the HDR image generating unit 42 and the color correcting unit 44, an imaging signal of the latest frame and an imaging signal, stored in the storage unit 46, one frame prior to the latest frame. In the present embodiment, the imaging signal acquiring unit 41 outputs, to the HDR image generating unit 42 and the color correcting unit 44, a first imaging signal including the long exposure image (first image data) captured with the first exposure amount and a second imaging signal, including the short exposure image (second image data) captured with the second exposure amount, of a frame prior to or subsequent to the first imaging signal. When one of a long exposure image and a short exposure image is an input image, the other is a stored image stored in the storage unit 46.

The HDR image generating unit 42 acquires, from the imaging signal acquiring unit 41, the first and second imaging signals including images having different exposure amounts generated by the imaging element 244 and generates an HDR image signal including HDR images $P_H1$ to $P_H4$ (e.g. the number of bits per channel is 32 bits) dynamic ranges of which are expanded by combining images having different exposure amounts. The HDR image generating unit 42 includes a weighted addition unit 421 which generates an HDR image signal by performing weighted addition processing of the first imaging signal and the second imaging signal and a weighted addition coefficient calculating unit 422 which calculates a weighted addition coefficient used for weighted addition processing by the weighted addition unit 421.

The weighted addition unit 421 outputs, to the tone compressing unit 43, the HDR image signal generated by performing weighted addition processing of the first imaging signal and the second imaging signal. Specifically, when the weighted addition unit 421 represents a position of each pixel as an orthogonal coordinate system (x, y), a pixel value of a long exposure image in the first imaging signal $S_L$ is denoted as L(x, y), a pixel value of a short exposure image in the second imaging signal $S_S$ is denoted as S(x, y), the weighted addition coefficient is denoted as α(x, y) (0<α(x, y)<1), and a pixel value of an HDR image in an HDR image signal $S_H$ is denoted as H(x, y), the pixel value H(x, y) of an HDR image is derived from the following mathematical formula (1). Note that descriptions are given below assuming that the weighted addition coefficient α is set to a short exposure image.

$$H(x,y)=(1-\alpha(x,y))\times L(x,y)+\alpha(x,y)\times \beta \times S(x,y) \quad (1)$$

The letter β is a coefficient acting on short exposure for adjustment of a difference in the exposure amount between short exposure and long exposure. The letter β is represented by $\beta=E_2/E_1$ where an exposure amount of short exposure processing is denoted as $E_1$ and an exposure amount of long exposure processing is denoted as $E_2$. Note that, when this coefficient acts on long exposure, a coefficient β' is represented by $\beta'=E_1/E_2$.

The weighted addition coefficient calculating unit 422 sets the weighted addition coefficient α(x, y) according to brightness (pixel value L(x, y)) of the long exposure image. Specifically, the weighted addition coefficient calculating unit 422 refers to the storage unit 46 and sets a larger value to the weighted addition coefficient α(x, y) as the pixel value L(x, y) of the long exposure image is larger than a preset reference value or sets a smaller value to the weighted addition coefficient α(x, y) as the pixel value L(x, y) of the long exposure image is smaller than the reference value. The weighted addition coefficient calculating unit 422 sets a weighted addition coefficient α(x, y) for each pixel position (coordinate). Note that the weighted addition coefficient calculating unit 422 sets the respective coefficients such that the sum of the weighted addition coefficient (first coefficient) of the pixel value S(x, y) and the weighted addition coefficient (second coefficient) of the pixel value L(x, y) equals one.

The tone compressing unit 43 generates a tone-compressed image signal $S_T$ (first tone-compressed image signal) including tone-compressed images $P_T1$ to $P_T4$ (tone mapping images) dynamic ranges of which are reduced to a size that can be displayed on the display device 5 by performing tone compression processing, for example processing to reduce the number of bits per channel from 32 bits to 12 bits, on the HDR image signal $S_H$ generated by the HDR image generating unit 42.

The color correcting unit 44 generates a color-corrected image signal $S_{T'}$ including a color-corrected image by performing color correcting processing on the first imaging signal $S_L$ and the second imaging signal $S_S$ based on the first imaging signal $S_L$ and the second imaging signal $S_S$ input from the imaging signal acquiring unit 41, the tone-compressed image signal $S_T$ generated by the tone compressing unit 43, and the weighted addition coefficient α(x, y).

The color correcting unit 44 includes: a luminance component extracting unit 441 which extracts a luminance component from each of the first imaging signal $S_L$, the second imaging signal $S_S$, and the tone-compressed image signal $S_T$; a gain map calculating unit 442 which calculates a gain map from the luminance components extracted by the luminance component extracting unit 441 and the weighted addition coefficient α(x, y); and a recombining processing unit 443 which generates a corrected HDR image signal where the first imaging signal $S_L$ and the second imaging signal $S_S$ are recombined after correcting a pixel value of each pixel based on the gain map and then generates the color-corrected image signal $S_{T'}$ (second tone-compressed image signal) including a color-corrected image that is a corrected tone-compressed image by performing tone compression processing on the corrected HDR image signal.

The luminance component extracting unit 441 performs, on the first imaging signal $S_L$, the second imaging signal $S_S$, and the tone-compressed image signal $S_T$, YCbCr conversion processing of a value represented in RGB into a luminance (Y) component and a color difference (CrCb) component and thereby extracts a luminance (Y) component of each of the signals. The luminance component extracting unit 441 outputs, to the gain map calculating unit 442, a luminance component signal $Y_L$ including a luminance component extracted from the first imaging signal $S_L$, a luminance component signal $Y_S$ including a luminance component extracted from the second imaging signal $S_S$, and a luminance component signal $Y_T$ including a luminance component extracted from the tone-compressed image signal $S_T$.

The gain map calculating unit 442 calculates a gain map based on the luminance components extracted by the luminance component extracting unit 441 and the weighted addition coefficient α(x, y). Specifically, when a gain value at a pixel position (x, y) in the first imaging signal $S_L$ is denoted as $G_L(x, y)$, a gain value at a pixel position (x, y) in the second imaging signal $S_S$ is denoted as $G_S(x, y)$, a luminance component of a pixel value L(x, y) of a long exposure image in the first imaging signal $S_L$ is denoted as $Y_L(x, y)$, a luminance component of a pixel value S(x, y) of a short exposure image in the second imaging signal $S_S$ is denoted as $Y_S(x, y)$, and a luminance component of a pixel value T(x, y) of a tone-compressed image in the tone-compressed image signal $S_T$ is denoted as $Y_T(x, y)$, the gain value $G_L(x, y)$ is derived from the following mathematical formula (2) and the gain value $G_S(x, y)$ is derived from the following mathematical formula (3).

$$G_L(x,y)=(1-\alpha(x,y))\times Y_T(x,y)/Y_L(x,y) \quad (2)$$

$$G_S(x,y)=\alpha(x,y)\times Y_T(x,y)/Y_S(x,y) \quad (3)$$

The gain map calculating unit 442 calculates a first gain map $G_L$ in which the gain value $G_L(x, y)$ is given to each pixel position and a second gain map $G_S$ in which the gain value $G_S(x, y)$ is given to each pixel position from the above mathematical formulas (2) and (3). The gain map calculating unit 442 outputs the calculated first gain map $G_L$ and the second gain map $G_S$ to the recombining processing unit 443.

The recombining processing unit 443 generates a corrected HDR image signal $S_Q$ where the first imaging signal $S_L$ and the second imaging signal $S_S$ are recombined after correcting a pixel value of each pixel based on the first gain map $G_L$ and the second gain map $G_S$ calculated by the gain map calculating unit 442 and then generates the color-corrected image signal $S_{T'}$ including a color-corrected image that is a corrected tone-compressed image by performing tone compression processing on the corrected HDR image signal $S_Q$. Specifically, when the recombining processing unit 443 denotes a pixel value of the corrected HDR image in the corrected HDR image signal $S_O$ as Q(x, y), the pixel value Q(x, y) is derived from the following mathematical formula (4).

$$Q(x,y)=G_L(x,y)\times L(x,y)+G_S(x,y)\times S(x,y) \qquad (4)$$

The recombining processing unit 443 generates the corrected HDR image signal $S_O$ by calculating the pixel value Q(x, y) based on the first gain map $G_L$ and the second gain map $G_S$ and then generates the color-corrected image signal $S_{T'}$ including color-corrected images $P_C1$ to $P_C4$ that are corrected tone-compressed images by performing tone compression processing on the corrected HDR image signal $S_O$. These color-corrected images are the aforementioned tone-compressed images (tone mapping images) performed with color-correction processing.

The color correcting unit 44 performs, on the color-corrected image signal $S_{T'}$ including the generated color-corrected images, optical black subtracting processing, white balance adjusting processing, color matrix operation processing, gamma correcting processing, color reproduction processing, edge enhancement processing, format conversion processing, or other processing and then outputs the processed color-corrected image signal $S_{T'}$ to the display device 5.

The input unit 45 receives input of various signals such as an operation command signal commanding operation of the endoscope system 1.

The storage unit 46 is implemented by a semiconductor memory such as a flash memory or a dynamic random access memory (DRAM). The storage unit 46 stores data including various programs for causing the endoscope system 1 to operate and various parameters required for operation of the endoscope system 1. The storage unit 46 further stores identification information of the processing device 4. The identification information includes unique information (ID), year of manufacture, and specification information, or the like of the processing device 4.

The storage unit 46 stores image data of images corresponding to imaging signals performed with signal processing by the imaging signal acquiring unit 41 such as a long exposure image captured by the first exposure processing or a short exposure image captured by the second exposure processing, a reference value of the weighted addition coefficient used upon weighted addition processing by the weighted addition unit 421, increase and decrease ratios of the weighted addition coefficient relative to the reference value, or other data. The storage unit 46 may include a ring buffer which stores the first and second imaging signals, for example. In this case, the ring buffer stores a predetermined number of frames from the latest imaging signal in a time series by overwriting the oldest imaging signal with the latest imaging signal when a capacity is in shortage (when imaging signals of a predetermined number of frames are stored).

The control unit 47 is configured by a central processing unit (CPU) or the like. The control unit 47 performs driving control of the respective components including the imaging element 244 and the light source device 3 as well as input and output control of information with the respective components. The control unit 47 refers to control information data (e.g. timing of reading) for imaging control stored in the storage unit 46 and transmits to the imaging element 244 via a predetermined signal wire included in the collective cable 245.

The control unit 47 further sets the exposure amount by detecting brightness from an image based on an acquired imaging signal and generates a control signal to cause the light source 31a to emit light of an amount (including intensity and duration) corresponding to the set exposure amount.

The display device 5 displays the color-corrected images $P_C1$ to $P_C4$ corresponding to the color-corrected image signal $S_{T'}$ generated by the processing device 4 (color correcting unit 44) via a video cable. The display device 5 includes a monitor such as liquid crystal or organic electroluminescence (EL).

In the endoscope system 1 described above, on the basis of an imaging signal input to the processing device 4, the HDR image generating unit 42 generates the HDR image signal $S_H$ from the first and second imaging signals (imaging signals $S_L$ and $S_S$) having different exposure amounts and then the tone compressing unit 43 generates the tone-compressed image signal $S_T$. Thereafter the color correcting unit 44 calculates the gain maps $G_L$ and $G_S$ based on the luminance (Y) component of each of the images of the imaging signals $S_L$ and $S_S$ and the tone-compressed image signal $S_T$, restructures a tone-compressed image signal performed with color correction based on the calculated gain maps $G_L$ and $G_S$, and thereby generates the color-corrected image signal $S_{T'}$. The display device 5 then displays a color-corrected image (color-corrected images $P_C1$ to $P_C4$) based on the restructured color-corrected image signal $S_{T'}$.

According to the embodiment of the disclosure described above, the HDR image signal is generated from the first and second imaging signals having different exposure amounts (brightness) and then the tone-compressed image signal is generated. Thereafter the gain maps are calculated based on the luminance component of each of the images of the first and second imaging signals and the tone-compressed image signal and a tone-compressed image performed with color correction based on the calculated gain maps is restructured. Therefore, even in the case of performing tone-compression, deterioration of reproducibility of colors of the tone-compressed image relative to the input image can be suppressed.

Note that, in the embodiment described above, descriptions are given assuming that the gain maps are calculated from the luminance (Y) component using the luminance (Y) component as a representative value based on an YCbCr color space; however, not limited to the YCbCr color space, the gain maps may be calculated by classifying into colors and luminance and using information of luminance and an HSV color space formed by three components of hue, saturation chroma, and value lightness brightness or an L*a*b* color space using a three-dimensional space. For example in the case of using the L*a*b* color space, tristimulus values (Y component in an XYZ space (three-dimensional space)) are used as representative values.

Note that, in the embodiment described above, descriptions are given assuming that the weighted addition coefficient α is set to a short exposure image; however, this may be set to a long exposure image.

Note that, in the embodiment described above, descriptions are given assuming that imaging signals generated by two different types of exposure processing are used; however, imaging signals generated by three or more types of exposure processing may be used.

Moreover, in the embodiment described above, color correcting processing after tone-compression may be switchable between execution and non-execution. This switchover may be performed based on command input by operation of a switch or the like by a user or may be automatically switchable by analyzing a captured image. When determination on switchover is made by image analysis, for example a difference in brightness and darkness of the image is calculated based on a luminance distribution of the image. If the calculation result is larger than a preset difference in brightness and darkness, color correcting processing may be executed. If the calculation result is less than or equal to the preset difference in brightness and darkness, the processing may not be executed.

In the embodiment described above, descriptions are given assuming that the light source device 3 is a separate body from the processing device 4; however, the light source device 3 and the processing device 4 may be integrated and for example the illumination unit 31 and the illumination control unit 32 may be included inside the processing device 4.

Note that, in the embodiment described above, descriptions are given assuming that the image processing device according to the disclosure functions as the HDR image generating unit 42, the tone compressing unit 43, and the color correcting unit 44 of the endoscope system 1 using the endoscope 2 an observation target of which is a biological tissue or the like in a subject; however, the disclosure is also applicable to an endoscope for industrial use that observes characteristics of a material or an endoscope system using an endoscope of a capsule type. The image processing device according to the disclosure is applicable regardless of inside or outside the body.

Note that, in the embodiment described above, descriptions are given with the example of the endoscope system; however, the disclosure is also applicable to a case where video is output to an electronic view finder (EVF) included in a digital still camera or the like, for example. In this case, as compared to a case of using an optical finder, it is possible to enhance visibility of an object while color tones of the original image is reproduced even when a difference in brightness and darkness in a scene is large such as in a backlight state.

Some embodiments achieves an effect of suppressing deterioration of reproducibility of colors of a tone-compressed image relative to an input image even when input images having different brightness are combined and tone-compressed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging system comprising:
an image sensor comprising a plurality of pixels configured to perform photoelectric conversion of external light to generate a first image signal of a first image and a second image signal of a second image, wherein the first image has a first dynamic range and the second image has a second dynamic range; and
a central processing unit (CPU) configured to:
generate a high dynamic range (HDR) image signal of an HDR image by performing a first HDR combining of the first image signal of the first image and the second image signal of the second image, wherein the HDR image has a first HDR that is greater than either of the first dynamic range or the second dynamic range;
generate a first tone-compressed image signal of a first tone-compressed image by performing a first tone compression processing on the HDR image signal, wherein the first tone-compressed image has a first compressed dynamic range that is lower than the first HDR; and
generate a color-corrected HDR image signal of a color-corrected HDR image by performing a second HDR combining of at least the first image signal and the second image signal based on the first tone-compressed image signal, wherein the color-corrected HDR image has a second dynamic range that is greater than either of the first dynamic range or the second dynamic range,
wherein the central processing unit is configured to:
generate the HDR image signal of the HDR image based on a value calculated by multiplying a pixel value of the first image signal by a first coefficient larger than zero and smaller than one, and a value calculated by multiplying a pixel value of the second image signal by a second coefficient a sum of which with the first coefficient equals one; and
generate the color-corrected HDR image signal by performing the second HDR combining of at least the first image signal and the second image signal based on the first tone-compressed image signal, and the first coefficient and the second coefficient,
wherein the central processing unit is configured to:
calculate a gain map corresponding to a pixel position by calculating a first gain value using a representative value of the first image signal, a representative value of the first tone-compressed image signal, and the first coefficient and by calculating a second gain value using a representative value of the second image signal, a representative value of the first tone-compressed image signal, and the second coefficient;
generate a corrected HDR image signal by performing the second HDR combining of at least the first image signal and the second image signal based on the gain map; and
generate the color-corrected HDR image signal of the color-corrected HDR image by performing tone compression processing on the corrected HDR image signal, and
wherein the central processing unit is configured to calculate the gain map corresponding to a pixel position by calculating the first gain value by multiplying the first coefficient by a ratio of the representative value of the first tone-compressed image signal to the representative value of the first image signal and by calculating the second gain value by multiplying the second coefficient by a ratio of the representative value of the first tone-compressed image signal to the representative value of the second image signal.

* * * * *